(12) United States Patent
Bar-Shalom

(10) Patent No.: US 6,787,156 B1
(45) Date of Patent: Sep. 7, 2004

(54) CONTROLLED RELEASE COMPOSITION

(75) Inventor: Daniel Bar-Shalom, Kokkedal (DK)

(73) Assignee: BM Research A/S, Vaerlose (DK)

( * ) Notice: Subject to any disclaimer, the term of this patent is extended or adjusted under 35 U.S.C. 154(b) by 0 days.

(21) Appl. No.: 08/693,254

(22) PCT Filed: Feb. 23, 1995

(86) PCT No.: PCT/DK95/00080

§ 371 (c)(1), (2), (4) Date: Aug. 19, 1996

(87) PCT Pub. No.: WO95/22962

PCT Pub. Date: Aug. 31, 1995

(30) Foreign Application Priority Data

Feb. 23, 1994 (DK) .............................................. 0222/94

(51) Int. Cl.[7] .......................... A61K 9/36; A61K 9/24; A61K 47/34; A61K 47/38
(52) U.S. Cl. ....................................... 424/480; 424/473
(58) Field of Search ................................ 424/486, 480, 424/473, 494, 426, 488

(56) References Cited

U.S. PATENT DOCUMENTS 4,330,338 A * 5/1982 Banker
4,786,505 A * 11/1988 Lovgren et al. ............ 424/480
5,422,123 A * 6/1995 Conte et al.

FOREIGN PATENT DOCUMENTS

| EP | 2332484 C2 | 1/1974 |
|---|---|---|
| EP | 2415490 | 10/1974 |
| WO | WO89/09066 | 10/1989 |
| WO | WO91/04015 | 4/1991 |

* cited by examiner

Primary Examiner—Edward J. Webman
(74) Attorney, Agent, or Firm—Beth A. Burrous; Foley & Lardner

(57) ABSTRACT

A composition for controlled delivery of at least one active substance into an aqueous medium by erosion at a preprogrammed rate of at least one surface of the composition, comprising the active substance, the matrix being erodible in the aqueous medium in which the composition is to be used, and a coating having at least one opening exposing at least one surface of said matrix, the coating comprising a first cellulose derivative which has thermoplastic properties and which is substantially insoluble in the aqueous medium in which the composition is to be used, and at least one of a second cellulose derivative which is soluble or dispersible in water, a plasticizer, and a filler. The coating is a coating which crumbles and/or erodes upon exposure to the aqueous medium such as a body fluid. The first cellulose derivative may be, e.g., ethycellulose, cellulose acetate, cellulose propionate or cellulose nitrate, and the second cellulose derivative may be, e.g., methylcellulose, carboxymethylcellulose or salts thereof, cellulose acetate phthalate, microcrystalline cellulose, ethylhydroxyethylcellulose, ethylmethylcellulose, hydroxyetylcellulose, hydroxyethylmethyl-cellulose, hydroxypropylcellulose, hydroxypropylmethylcellulose, hydroxymethylcellulose or hydroxymethylpropylcellulose.

47 Claims, No Drawings

CONTROLLED RELEASE COMPOSITION

FIELD OF THE INVENTION

The present invention relates to a composition for controlled delivery of an active substance into an aqueous medium.

BACKGROUND OF THE INVENTION

It is known to obtain sustained release of an active substance, e.g. a pharmaceutically active powder, by embedding it in a matrix of an insoluble substance from which the active substance will gradually diffuse. Sustained release of an active substance contained in a tablet core may also be achieved by applying to the core a semi-permeable coating through which water and dissolved active substance may diffuse or an insoluble coating provided with a hole through which the active substance is released. Gradual release of an active substance may furthermore be obtained by microencapsulating particles of an active substance in one or more layers of film which may be of different types, e.g. of a type which mediates diffusion of the active substance or release thereof in the intestines.

These conventional ways of providing sustained release of an active substance have certain drawbacks, in that it is difficult to maintain a constant concentration of the active substance, for example a constant concentration of a pharmaceutically active substance in plasma for the entire period when the dosage form is present in the body. In particular, this may be the problem with drugs which have a brief half-life in the body. Furthermore, the penetration of water through diffusion coatings may cause hydrolysis of active substances which are unstable in an aqueous environment.

WO 89/09066 discloses a composition for controlled delivery of an active substance into an aqueous phase by erosion at a substantially constant rate of a surface or surfaces of the composition, the composition containing a) a matrix of a crystalline polyethylene glycol polymer with a molecular weight of at least 20,000 daltons, b) at least one non-ionic emulsifier dispersed in the polyethylene glycol matrix in an amount of 2–50% by weight of the crystalline polymer and the non-ionic emulsifier, the non-ionic emulsifier having at least one domain which is compatible with the polyethylene glycol polymer and being selected from fatty acid esters and fatty alcohol ethers, and c) at least one active substance substantially homogeneously dispersed in the polyethylene glycol matrix and/or located in geometrically well-defined zones within the composition, the non-ionic emulsifier and/or the active substance reducing the water affinity of domains between grains and in cracks in the crystalline polymer matrix and in the crystalline polymer matrix itself, thereby substantially eliminating water diffusion in the interface between the polymer crystals, so that the erosion is predominantly effected by the dissolving action of an aqueous medium on a surface or surfaces of the composition exposed to the medium.

Other controlled release compositions based on this principle are disclosed in WO 91/04015, which relates to compositions that provide a regulated non-initial burst release of an active substance at a predetermined time.

The present invention is a further development based on the inventions disclosed in WO 89/09066 and WO 91/04015. In particular, the present invention provides a novel coating based on certain cellulose derivatives, the coating being particularly suitable for controlled release compositions with a matrix containing an active substance, e.g. a matrix such as that disclosed WO 89/09066.

SUMMARY OF THE INVENTION

The present invention thus relates to a composition for controlled delivery of at least one active substance into an aqueous medium by erosion at a preprogrammed rate of at least one surface of the composition, comprising i) a matrix comprising the active substance, the matrix being erodible in the aqueous medium in which the composition is to be used, and ii) a coating having at least one opening exposing at least one surface of said matrix, the coating comprising a) a first cellulose derivative which has thermoplastic properties and which is substantially insoluble in the aqueous medium in which the composition is to be used, and at least one of b) a second cellulose derivative which is soluble or dispersible in water, c) a plasticizer, and d) a filler, said coating being a coating which crumbles and/or erodes upon exposure to the aqueous medium, in particular a body fluid, at a rate which is equal to or slower than the rate at which the matrix erodes in the aqueous medium, allowing exposure of said surface of the matrix to the aqueous medium to be controlled.

The combination of the matrix and the active substance must be substantially impenetrable to fluids of the aqueous phase, for example body fluids present where the composition of the invention is introduced into the body (e.g. in the gastrointestinal tract, including the rectum, in the vagina or subcutaneously) or into a body cavity via a catheter (e.g. the urinary bladder, the gall bladder, the uterus, a central nervous system cavity, infectious/malignant/post-operative cavities, etc.), in order to avoid degradation of the active substance residing in the matrix due to the action of water in the case of an active substance which is susceptible to hydrolysis. The inclusion of the active substance in a matrix into which water diffusion is substantially eliminated will thus impart stability to the composition, so that the active substance will remain active even when the composition has been exposed to body fluids or other fluids for a period of time. As the fluids can only act on the surface of a matrix of this type, the active substance embedded therein is only exposed to the fluids in question when it is released or immediately prior to its release from the matrix. A matrix of a type which is substantially impenetrable to water will therefore ensure the stability of the active substance in the matrix until the time when the active substance is actually released, and will also ensure that release of the active substance takes place at a controlled and reproducible rate, since the release proceeds gradually from the surface or surfaces of the matrix exposed to the fluids in question.

Due to the controlled release of the active substance from the composition of the invention, it is possible to obtain a substantially constant rate of release or a controlled pulsatile release of the active substance over a specific period of time. Adherence to a strict dosage regimen, e.g. requiring administration of a drug at set intervals up to several times a day, may therefore be dispensed with. Furthermore, it is possible to include two or more different active substances in the composition of the invention, adapted to be released at different concentrations and/or intervals, thus making it easier for patients to follow a prescribed regimen.

An additional advantage of the composition of the invention is that it may be produced by relatively simple and inexpensive methods, e.g. by extrusion, as will be explained in more detail below. Furthermore, the composition allows for the incorporation of high concentrations of the active substance relative to the composition's size. This is obviously a great advantage, notably when the composition is to be used for the delivery of a pharmaceutically active substance, since it allows for the delivery of the required amount of the active substance without the composition being unnecessarily large. Compositions of the invention in which the matrix contains a surface active agent may furthermore be used for the delivery of sparingly soluble or non-soluble pharmaceutical powders which can otherwise be difficult to administer, since such substances are compatible with the lipophilic domains of the surface active agent.

DETAILED DISCLOSURE OF THE INVENTION

A suitable matrix for use in the compositions of the invention is one of the type described in WO 89/09066 or WO 91/04015, to which reference is made and which are incorporated herein by reference, i.e. a matrix containing a crystalline polyethylene glycol polymer with a molecular weight of at least 20,000 daltons in which at least one non-ionic emulsifier is dispersed. A preferred non-ionic emulsifier for use in the matrix is polyethylene glycol stearate. Preferred polyethylene glycols for use in the matrix have a molecular weight in the range of 20,000–35,000 daltons. However, while WO 89/09066 discloses matrices containing a crystalline polyethylene glycol polymer with a molecular weight of at least 20,000 daltons, interesting compositions according to the present invention also include those in which the matrix contains a polyethylene glycol polymer with a molecular weight of less than 20,000 daltons.

The crystalline polymer matrix must have a melting point which is above the temperature of the aqueous medium in which the composition of the invention is to be used. Thus, the polymer(s) employed in the matrix will suitably have a melting point of about 20–120° C., typically about 30–100° C., more typically about 40–80° C., depending on how the composition is to be employed. In particular, when the composition of the invention is used for the delivery of a drug for human or veterinary use, the matrix will suitably have a melting point of about 40–80° C.

Alternatively, the matrix may be of the same basic type as the coating, i.e. comprising a thermoplastic and substantially insoluble cellulose derivative, e.g. ethylcellulose, as well as at least one other cellulose derivative and/or a plasticizer and/or a filler. In a matrix of this type the cellulose derivative(s), the plasticizer and the filler may be selected from the corresponding cellulose derivatives, plasticizers and fillers described below in connection with the coating. The specific compounds and amounts thereof used for the matrix in this case would of course have to be adapted to the particular coating used for any given composition, so that the desired erosion pattern and release of the active substance into the aqueous medium is obtained.

As mentioned above, the coating is one which crumbles and/or erodes upon exposure to an aqueous medium at a rate which is equal to or slower than the rate at which the matrix erodes in the same aqueous medium. Exposure of the surface of the matrix to the aqueous medium is thereby controlled, so that the desired release profile of the active substance in the matrix is obtained.

As mentioned above, the first cellulose derivative is one which has thermoplastic properties, i.e. it softens upon heating. The first cellulose derivative may be a cellulose ether which, when heated, is shapeable by molding or extrusion, including injection molding, blow molding and compression molding. A preferred cellulose ether is ethylcellulose, typically an ethylcellulose with an ethoxyl content in the range of 44.5–52.5%, such as in the range of 45.0–46.5% or in the range of 48.0–49.5%. Typical commercially available ethylcellulose products have an ethoxyl content of 45.0–49.5%, corresponding to 2.25–2.85 ethoxyl groups per anhydroglucose unit.

The first cellulose derivative may furthermore be selected from the group consisting of cellulose acetate, cellulose propionate and cellulose nitrate.

The second cellulose derivative is typically selected from the group consisting of methylcellulose, carboxymethylcellulose and salts thereof, cellulose acetate phthalate, microcrystalline cellulose, ethylhydroxyethylcellulose, ethylmethylcellulose, hydroxyethylcellulose, hydroxyethylmethylcellulose, hydroxypropylcellulose, hydroxypropylmethylcellulose, hydroxymethylcellulose and hydroxymethylpropylcellulose. When the second cellulose derivative is a salt of carboxymethylcellulose, the salt will typically be selected from the group consisting of alkali metal and alkaline earth metal salts.

Currently preferred compounds for use as the second cellulose derivative pharmaceutical quality hydroxypropylmethylcellulose or carboxymethylcellulose.

The use of a plasticizer will often be desirable in order to improve the processibility of the ethylcellulose or other first cellulose derivative, e.g. to adjust the softening point of the ethylcellulose. When the coating contains a plasticizer, this is typically selected from the group consisting of phosphate esters; phthlalate esters; amides; mineral oils; fatty acids and esters thereof with polyethylene glycol, glycerin or sugars; fatty alcohols and ethers thereof with polyethylene glycol, glycerin or sugars; and vegetable oils. Suitable fatty alcohols are cetostearyl alcohol, cetyl alcohol, stearyl alcohol, oleyl alcohol and myristyl alcohol.

The plasticizer may also be a non-ionic surfactant, e.g. a non-ionic surfactant is selected from the group consisting of diacetylated monoglycerides, diethylene glycol monostearate, ethylene glycol monostearate, glyceryl monooleate, glyceryl monostearate, propylene glycol monostearate, macrogol esters, macrogol stearate 400, macrogol stearate 2000, polyoxyethylene 50 stearate, macrogol ethers, cetomacrogol 1000, lauromacrogols, nonoxinols, octoxinols, tyloxapol, poloxamers, polyvinyl alcohols, polysorbate 20, polysorbate 40, polysorbate 60, polysorbate 65, polysorbate 80, polysorbate 85, sorbitan monolaurate, sorbitan monooleate, sorbitan monopalmitate, sorbitan monostearate, sorbitan sesquioleate, sorbitan trioleate, sorbitan tristearate and sucrose esters.

The plasticizer may further be selected from the group consisting of methyl abietate, acetyl tributyl citrate, acetyl triethyl citrate, diisooctyl adipate, amyl oleate, butyl ricinoleate, benzyl benzoate, butyl and glycol esters of fatty acids, butyl diglycol carbonate, butyl oleate, butyl stearate, di($\beta$-methoxyethyl) adipate, dibutyl sebacate, dibutyl tartrace, diisobutyl adipate, dihexyl adipate, triethylene glycol di(2-ethyl butyrate), polyethylene glycol di(2-ethyl hexoate), diethylene glycol monolaurate, monomeric polyethylene ester, hydrogenated methyl ester of rosin, methoxyethyl oleate, butoxyethyl stearate, butyl phthalyl butyl glycolate, glycerol tributyrate, triethylene glycol dipelargonate, $\beta$-(p-tert.-amylphenoxy)ethanol, $\beta$(p-tert.-butylphenoxy)ethanol, $\beta$-(p-tert.-butylphenoxyethyl)-acetate, bis($\beta$-p-tert.-butylphenoxydiethyl)ether, camphor, Cumar W-1, Cumar MH-1, Cumar V-1, diamyl phthalate, (diamylphenoxy)ethanol, diphenyl oxide, technical hydrobietyalcohol, beckolin, benzene hexahydrochloride, Clorafin® 40, Piccolasrice® A-5, Piccolastic® A-25, Flexol B-400, Glycerol α-methyl α-phenyl ether, chlorinated naphthalene, HB-40, monoamylphthalate, Nevillac 10. o-nitro-diphenyl and Paracril 26.

When the coating contains a filler, the filler is preferably a conventional tablet or capsule excipient such as a diluent, a binder, a lubricant or a disintegrant.

Diluents for use as fillers may be selected from the group consisting of dicalcium phosphate, calcium sulfate, sugars, including lactose and sucrose, dextrin, cellulose, cellulose derivatives, kaolin, mannitol, dry starch, glucose, sorbitol, and inositol.

Suitable binders are those selected from the group consisting of acacia, sodium alginate, starch, gelatin, saccharides, including glucose, sucrose, dextrose and lactose, molasses, extract of Irish moss, panwar gum, ghatti gum, mucilage of isapol husk, carboxymethylcellulose, methylcellulose, veegur, larch arabolactan, polyethylene glycols, ethylcellulose, water, alcohols, waxes, and polyvinylpyrrolidone.

Suitable lubricants are those selected from the group consisting of talc, magnesium stearate, calcium stearate, stearic acid, hydrogenated vegetable oils, sodium benzoate, sodium chloride, leucine, carbowax 4000, magnesium lauryl sulfate, and colloidal silicon dioxide.

Suitable disintegrants are those selected from the group consisting of starches, clays, cellulose derivatives including croscarmellose, gums, algins, combinations of hydrocarbonates with weak acids, crospovidone, sodium starch glycolate, agar, cation exchange resins, citrus pulp, veegum HV, natural sponge, and bentonite.

Compositions according to the invention may further comprise a water soluble antioxidant, a lipid soluble antioxidant and/or a preservative in either the matrix or the coating. Suitable antioxidants and preservatives may be selected from the group consisting of ascorbyl palmitate, benzoic acid, benzyl hydroxybenzoate, bronopol, butyl hydroxybenzoate, butylated hydroxyanisole, butylated hydroxytoluene, chlorbutol, cinnamic acid, dehydroacetic acid, diethyl pyrocarbonate, diphenyl, dodecyl gallate, ethoxyquin, ethyl gallate, ethyl hydroxybenzoate, gallic acid, isoascorbic acid, methyl hydroxybenzoate, monothioglycerol, nordihydroguaiaretic acid, octyl gallate, pentachlorophenol, phenethyl alcohol, phenoxyethanol, phenylmercuric acetate, phenylmercuric borate, phenylmercuric nitrate, o-phenylphenol, potassium metabisulphite, potassium sorbate, propyl gallate, propyl hydroxybenzoate, sodium benzoate, sodium butyl hydroxybenzoate, sodium dehydroacetate, sodium diacetate, sodium ethyl hydroxybenzoate, sodium formaldehyde sulphoxylate, sodium isoascorbate, sodium metabisulphite, sodium methyl hydroxybenzoate, sodium o-phenylphenol, sodium propyl hydroxybenzoate, sodium sulphite, anhydrous sodium sulphite, sorbic acid, sulphur dioxide, and thiodipropionic acid.

The coating may be designed so that its longitudinal erosion rate is substantially the same as the longitudinal erosion rate of the matrix, whereby the matrix and the coating will erode longitudinally towards the center of the composition at substantially the same rate. Such a coating would be suitable for a rod-shaped composition having an opening in the coating at each end. Thus, when the matrix has been completely eroded by the aqueous medium, the coating will also be substantially completely eroded. A composition having such a coating has the advantage of being completely biodegraded upon release of the active substance.

The coating may also be in which, in the aqueous medium in which the composition is to be used, the coating does not completely crumble or erode before the matrix has completely eroded. A coating of this type would remain more or less intact as long as it was supported by the matrix containing the active substance, but it would lack the ability to remain intact after erosion of the matrix, whereby it would then disintegrate or crumble, so that it would not remain in e.g. a human or animal for any significant amount of time after the complete erosion of the matrix and the release of the active substance.

The active substance to be delivered by the composition according to the invention can be a drug for human or veterinary use, a vitamin or other nutritional supplement, a disinfectant, a deodorant or another substance to be administered continuously in an aqueous environment.

The composition of the invention is especially suitable for the delivery of an active substance which is a pharmaceutically active substance, in particular a pharmaceutically active powder. The pharmaceutically active substance or substances included in the composition of the invention may be selected from many therapeutic categories, in particular from substances which may advantageously be administered orally, rectally, vaginally or subcutaneously, or administered to a body cavity (e.g. the urinary bladder, the gall bladder, the uterus, a central nervous system cavity, infectious/malignant/post-operative cavities, etc.). Examples of such substances are antimicrobial agents, analgesics, antiinflammatory agents, counter irritants coagulation modifying agents, diuretics, sympathomimetics, anorexics, antacids and other gastrointestinal agents, antiparasitics, antidepressants, antihypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, parasympathomimetics, anticonvulsants, antihistamines, β-blockers, purgatives, antiarrhytmics, contrast materials, radiopharmaceuticals, antiallergic agents, tranquilizers, vasodilators, antiviral agents, and antineoplastic or cytostatic agents or other agents with anticancer properties, or a combination thereof. Other suitable active substances may be selected from contraceptives and vitamins as well as micro- and macronutrients.

The composition is in addition suitable for the delivery of polypeptides, for example hormones such as growth hormones, enzymes such as lipases, proteases, carbohydrases, amylases, lactoferrin, lactoperoxidases, lysozymes, nanoparticles, etc., and antibodies. The composition may also be employed for the delivery of microorganisms, either living, attenuated or dead, for example bacteria, e.g. gastrointestinal bacteria such as streptococci, e.g. *S. faecium*, Bacillus. spp. such as *B. subtilis* and *B. licheniformis*, lactobacteria, Aspergillus spp., bifidogenic factors, or viruses such as indigenous vira, enterovira, bacteriophages, e.g. as vaccines, and fungi such as baker's yeast, *Saccharomyces cerevisiae* and fungi imperfect. The composition may also be used for the delivery of active agents in specialized carriers such as liposomes, cyclodextrines, nanoparticles, micelles and fats.

One of the uses for which the composition of the invention is well-suited is the delivery of antimicrobial agents to the vagina. Examples of such agents are antifungals, for example imidazole antifungals such as clotrimazole, econazol, ketoconazole and miconazole, polyene antifungal antibiotics such as nystatin, and antiprotozoals such as metronidazole and oxadiazole.

A pharmaceutically active powder to be administered by the composition of the invention will suitably have a particle size of from about 0.1 µm to about 500 µm, typically from about 0.5 µm to about 300 µm, more typically from about 1 µm to about 200 µm, especially from about 5 µm to about 100 µm.

The active substance will suitably be present in an amount of up to about 60%, typically up to about 50%, by weight of the composition. An active substance content of about 70% is contemplated to be the maximum content which still allows for a sufficient content of the crystalline polymer matrix and the non-ionic emulsifier in the composition. The active substance may, on the other hand, be present in the composition in much smaller amounts, depending on the nature and strength of the active substance in question.

Diffusion of water into the composition is substantially limited to the surface layer of the matrix, whereby any exposed matrix surfaces are eroded at a substantially constant and pH-independent rate. As a result, a substantially zero order release of the active substance is obtained, the term "zero order" referring to the fact that the release rate of the active substance is substantially constant with time, when the active substance is substantially homogeneously distributed in the matrix. In the case of the active substance being located in geometrically well-defined zones within the matrix, the result of the constant erosion rate of the matrix will be a strictly controlled pulsatile release of the active ingredient.

The geometric form of the composition is important for the obtainment of the above-mentioned controlled zero order or pulsatile release. Thus, in a preferred version of the invention, the composition of the invention has a geometric shape which enables a substantially constant surface area to become exposed during erosion of the matrix. The composition may thus e.g. have the shape of a cylindrical rod provided with a cellulose derivative-based coating of the type described above.

While the composition will typically be in the form of a rod or cylinder, it may also have another shape which allows the active substance to be released at the desired preprogrammed rate. The term "cylindrical rod" as used in the context of the present invention is understood to comprise not only those geometrical forms having a substantially circular cross-section, but also other substantially cylindrical forms, e.g. those having a somewhat flattened cross-section, for example a substantially oval or ellipse shaped cross-section.

It will also be understood by a person skilled in the art that the specific finished form of the composition of the invention may comprise certain minor modifications in order to facilitate the use of the composition in question. For example, a cylindrical rod-shaped composition for delivery of a pharmaceutical powder may have rounded ends so as to avoid possible injury or discomfort when the composition is introduced into the body.

As mentioned above, the active substance can be substantially homogeneously dispersed in the crystalline polymer matrix, in which case a substantially zero order release of the active substance is obtained. Alternatively, a pulsatile release of the active substance may be obtained in a composition of the invention which comprises alternating layers.

A pulsatile release may thus be obtained with a composition having the above-mentioned shape of a cylindrical rod and comprising alternating substantially transverse layers of 1) a layer comprising the crystalline polymer matrix, and 2) a layer comprising the active ingredient. If desired, the active ingredient may also be dispersed in the crystalline polymer matrix. In a composition comprising alternating layers, the alternating layers may comprise two or more different active substances.

These two release patterns (i.e. zero order and pulsatile) may also be combined so that a uniform release of one active substance (for example at a fairly low dosage level) alternates with the release in bursts of the same or another active substance (for example at a higher dosage level).

The composition of the invention may be produced by various methods which are either known per se in the pharmaceutical industry or which, for example, are used in the production of polymer-based materials, depending upon the desired embodiment and the materials employed in the composition in question. As mentioned above, one advantage of the composition according to the invention is that it may be produced by methods which are relatively simple and inexpensive.

The composition may be produced by, for example, co-extrusion of the coating with the matrix and the active substance, extrusion and dip coating, injection molding and dip coating, or by extrusion or injection molding.

For the preparation of a composition having a matrix of a crystalline polymer and a non-ionic emulsifier, these ingredients will typically be mixed while heating at a temperature sufficient to melt the polymer, and while stirring, so as to obtain a substantially homogeneous mixture. In the case of the active substance being included in the matrix, it may either be added to the molten mixture of the polymer and the non-ionic emulsifier or it may be added to the mixture prior to heating. The molten mixture is then e.g. extruded or injected, as explained below. For the preparation of a composition for pulsatile release of the active substance, the active substance may conveniently be included in matrix material, the mixture of the active substance and the matrix material being e.g. extruded or injected inlayers which alternate with layers of the matrix without the active substance.

For the production of a composition which has the shape of a cylindrical rod, the matrix material comprising the active substance may be injected into a pre-formed tube which forms the coating. Alternatively, a cylindrical rod-shaped composition may be produced by infecting alternating layers comprising at least, respectively, the matrix material and the active substance into said tube. A cylindrical rod-shaped composition may also be produced by, for example, extruding the matrix material with the active substance dispersed therein, followed by dip coating; or by co-extrusion of a) the matrix material with the active substance dispersed therein and b) the coating.

A cylindrical rod shaped composition may also be produced by injection molding, including two-component or multiple-component injection molding, of the coating and the matrix comprising the active substance. Injection molding is especially suitable for the coatings used according to the present invention. Typically, a cylinder which functions as a coating is produced in a first step around a solid core of e.g. steel, after which the matrix is produced in a second step or, alternatively, multiple steps by injection of the matrix material after removal of the steel core. This method has the advantage of being simple and well-suited for mass production.

Production methods which involve co-extrusion are also advantageous, as they are also simple and inexpensive methods suitable for mass production. The rod or tube which is produced by co-extrusion or extrusion is then cut into smaller segments of an appropriate size. The composition may then be finished, for example by rounding the ends of the individual cylindrical rods.

It will be clear to persons skilled in the art that the amount of active substance and the dimensions and specific form of the composition of the invention will of course vary according to the nature of the active substance in question as well as the intended use of the composition. The particular dose to be administered to a person or animal when the composition is used for the delivery of a pharmaceutically active powder will thus depend on such factors as the condition and age of the patient and the particular condition to be treated.

The present invention is further illustrated by the following non-limiting examples.

EXAMPLE 1

A composition according to the invention was prepared from the following ingredients:

|  | % by weight |
| --- | --- |
| Coating |  |
| Ethylcellulose (Dow Chem. Co.) (ethoxyl content 45–46.5%) | 50 |
| Hydroxymethylcellulose | 20 |
| Carboxymethylcellulose | 5 |
| Cetostearyl alcohol | 20 |
| Titanium dioxide | 5 |
| Matrix |  |
| Polyethylene glycol 35,000 | 50 |
| Polyethylene glycol 2000 stearate | 10 |
| Potato starch | 39 |
| Tartrazine | 1 |

The coating was prepared by first mixing the ethylcellulose with the hydroxymethylcellulose, carboxymethylcellulose and titanium dioxide, after which melted cetostearyl alcohol was added. After mixing in a high speed dry mixer (Robot Coupe) for about 2 minutes, the mixture was dried in an oven at 100° C. for about 30 minutes. The mixture was then allowed to cool to room temperature, after which it had a suitable consistency for being fed into an injection moulding machine.

The matrix was prepared by first mixing the PEG 35,000, the potato starch and the tartrazine together in a high speed dry mixer (Robot Coupe). The PEG 2000 stearate was then melted on a heating plate at a temperature of 100° C. and added to the mixture of the other 3 ingredients while mixing. After mixing for 2 minutes the mixture was allowed to cool to room temperature and was ready to be fed into an injection moulding machine.

The composition was prepared by injection moulding (Arbourg Allrounder) using a single unit mould, resulting in a composition containing a cylindrical inner matrix with dimensions of 4×12 mm and a coating with thickness of 0.5 mm.

Both the coating and matrix mixtures were easy to feed into the injection moulding machine and performed well in the mould. An analysis of the dissolution of the composition prepared as above in a dissolution tester (U.S.-Paddle) with saline as an aqueous medium showed a zero order release of the tartrazine in the matrix over a period of 12 hours. After 24 hours the coating was slightly weakened and slightly eroded at the surface.

The same composition was then taken orally by volunteers and isolated in feces after a transit time of 16–48 hours. (A total of 8 units with varying passage times were evaluated). After passage through the gastrointestinal tract about 20–30% by weight of the coating of the composition had been eroded from its surface, and the coating was soft and weak. It is believed that a longer passage time (longer retention in the gastrointestinal tract) would result in the complete erosion/dissolution of the coating.

EXAMPLE 2

A composition according to the invention was prepared from the following ingredients:

|  | % by weight |
| --- | --- |
| Coating |  |
| Ethylcellulose (Dow Chem. Co.) (ethoxyl content 45–46.5%) | 50 |
| Hydroxymethylcellulose | 17.5 |
| Carboxymethylcellulose | 7.5 |
| Cetostearyl alcohol | 20 |
| Titanium dioxide | 5 |
| Matrix |  |
| Polyethylene glycol 35,000 | 37 |
| Polyethylene glycol 2000 stearate | 10 |
| Potato starch | 49 |
| Tartrazine | 1 |
| Hydroxymethylcellulose | 3 |

The coating was prepared as described above in Example 1.

The matrix was also prepared as described above in Example 1 the hydroxymethylcellulose being mixed together with the PEG 35,000, the potato starch and the tartrazine in the initial mixing step.

A composition having the same dimensions as that of Example 1 was prepared as described in Example 1.

Also the coating and matrix mixtures of this Example were easy to feed into the injection moulding machine and performed well in the mould. An analysis (using the method described in Example 1) of the dissolution of the composition showed a zero order release of the tartrazine in the matrix over a period of 28 hours. After 36 hours the coating was slightly eroded and weak, as was the case with the composition of Example 1. The erosion and weakening/softening of the coating after passage through the gastrointestinal tract of human volunteers was also of the same extent and character as observed with the coating of Example 1.

What is claimed is:

1. A composition for controlled delivery of at least one active substance into an aqueous medium by erosion of at least one surface of the composition, wherein said erosion occurs at a preprogrammed rate, comprising
    i) a matrix comprising the active substance, wherein the matrix is erodible in the aqueous medium in which the composition is used and wherein the matrix allows substantially no diffusion of water into the composition beyond any exposed surface layers of the matrix, and ii) a coating having at least one opening exposing at least one surface of said matrix, the coating comprising
a) a first cellulose derivative which has thermoplastic properties and which is substantially insoluble in the aqueous medium in which the composition is used, and at least one of
b) a second cellulose derivative which is soluble or dispersible in water,
c) a plasticizer, and
d) a filler,
wherein said coating crumbles and/or erodes upon exposure to the aqueous medium, at a rate which is equal to or slower than the rate at which the matrix erodes in the aqueous medium, allowing controlled exposure of said surface of the matrix to the aqueous medium.

2. A composition according to claim 1 wherein any exposed matrix surfaces erode at a substantially constant rate.

3. A composition according to claim 1 wherein, in the aqueous medium in which the composition is to be used, the coating does not completely crumble or erode before the matrix has completely eroded.

4. A composition according to claim 1 in which said first cellulose derivative is a cellulose ether which, when heated, is shapeable by molding or extrusion, including injection molding, blow molding and compression molding.

5. A composition according to claim 1, in which said first cellulose derivative is a cellulose ether comprising at least one ethylcellulose.

6. A composition according to claim 1, in which said first cellulose derivative is an ethylcellulose having an ethoxyl content in the range of 44.5–52.5%.

7. A composition according to claim 1, in which said first cellulose derivative is an ethylcellulose having an ethoxyl content in the range of 45.0–49.5%.

8. A composition according to claim 1 in which said first cellulose derivative is selected from the group consisting of cellulose acetate, cellulose propionate and cellulose nitrate.

9. A composition according to claim 1 in which said second cellulose derivative is selected from the group consisting of methylcellulose, carboxymethylcellulose and salts thereof, cellulose acetate phthalate, microcrystalline cellulose, ethylhydroxyethylcellulose, ethylmethylcellulose, hydroxyethylcellulose, hydroxyethylmethylcellulose, hydroxypropylcellulose, hydroxypropylmethylcellulose, hydroxymethylcellulose and hydroxymethylpropylcellulose.

10. A composition according to claim 1, in which said second cellulose derivative is a salt of carboxymethylcellulose which salt is selected from the group consisting of alkali metal and alkaline earth metal salts.

11. A composition according to claim 9 in which said second cellulose derivative is pharmaceutical quality hydroxypropylmethylcellulose.

12. A composition according to claim 1 in which said plasticizer is selected from the group consisting of phosphate esters; phthalate esters; amides; mineral oils; fatty acids and esters thereof with polyethylene glycol, glycerin or sugars; fatty alcohols and ethers thereof with polyethylene glycol, glycerin or sugars; and vegetable oils.

13. A composition according to claim 1 in which said plasticizer is a fatty alcohol which is selected from the group consisting of cetostearyl alcohol, cetyl alcohol, stearyl alcohol, oleyl alcohol and myristyl alcohol.

14. A composition according to claim 1 in which said plasticizer is a non-ionic surfactant.

15. A composition according to claim 1, in which said filler is selected from the group consisting of a diluent, a binder, a lubricant and a disintegrant.

16. A composition according to claim 1 in which the matrix and/or the coating further comprises a water soluble antioxidant, a lipid soluble antioxidant and/or a preservative.

17. A composition according to claim 1 in which the matrix comprises a crystalline polyethylene glycol polymer and at least one non-ionic emulsifier dispersed in the polyethylene glycol matrix in an amount of 2–50% by weight of the crystalline polymer and the non-ionic emulsifier, the non-ionic emulsifier having at least one domain which is compatible with the polyethylene glycol polymer and being selected from fatty acid esters and fatty alcohol ethers, the active substance being substantially homogeneously dispersed in the polyethylene glycol matrix and/or located in geometrically well-defined zones within the matrix, the non-ionic emulsifier and/or the active substance reducing the water affinity of domains between grains and in cracks in the crystalline polymer matrix and in the crystalline polymer matrix itself, thereby substantially eliminating water diffusion in the interface between the polymer crystals, so that erosion of the matrix is predominantly effected by the dissolving action of the aqueous medium on any matrix surfaces exposed to the medium.

18. A composition according to claim 1, in which the matrix comprises a crystalline polyethylene glycol polymer having a molecular weight of at least 20,000 daltons and at least one nonionic emulsifier dispersed in the polyethylene glycol matrix in an amount of 2–50% by weight of the crystalline polymer and the non-ionic emulsifier, the non-ionic emulsifier having at least one domain which is compatible with the polyethylene glycol polymer and being selected from fatty acid esters and fatty alcohol esters, the active substance being substantially homogeneously dispersed in the polyethylene glycol matrix and/or located in geometrically well-defined zones within the matrix, the non-ionic emulsifier and/or the active substance reducing the water affinity of domains between grains and in cracks in the crystalline polymer matrix and in the crystalline polymer matrix itself, thereby substantially eliminating water diffusion in the interface between the polymer crystals, so that erosion of the matrix is predominantly effected by the dissolving action of the aqueous medium on any matrix surfaces exposed to the medium.

19. A composition according to claim 1, in which the matrix comprises a crystalline polyethylene glycol polymer having a molecular weight in the range of 20,000–35,000 daltons and at least one non-ionic emulsifier dispersed in the polyethylene glycol matrix in an amount of 2–50% by weight of the crystalline polymer and the non-ionic emulsifier, the non-ionic emulsifier having at least one domain which is compatible with the polyethylene glycol polymer and being selected from fatty acid esters and fatty alcohol ethers, the active substance being substantially homogeneously dispersed in the polyethylene glycol matrix and/or located in geometrically well-defined zones within the matrix, the non-ionic emulsifier and/or the active substance reducing the water affinity of domains between grains and in cracks in the crystalline polymer matrix and in the crystalline polymer matrix itself, thereby substantially eliminating water diffusion in the interface between the polymer crystals, so that erosion of the matrix is predominantly effected by the dissolving action of the aqueous medium on any matrix surfaces exposed to the medium.

20. A composition according to claim 1, in which the matrix comprises a crystalline polyethylene glycol polymer having a molecular weight of less than 20,000 daltons and at least one non-ionic emulsifier dispersed in the polyethylene glycol matrix in an amount of 2–50% by weight of the crystalline polymer and the non-ionic emulsifier, the non-ionic emulsifier having at least one domain which is compatible with the polyethylene glycol polymer and being selected from fatty acid esters and fatty alcohol esters, the active substance being substantially homogeneously dispersed in the polyethylene glycol matrix and/or located in geometrically well-defined zones within the matrix, the non-ionic emulsifier and/or the active substance reducing the water affinity of domains between grains and in cracks in the crystalline polymer matrix and in the crystalline polymer matrix itself, thereby substantially eliminating water diffusion in the interface between the polymer crystals, so that erosion of the matrix is predominantly effected by the dissolving action of the aqueous medium on any matrix surfaces exposed to the medium.

21. A composition according to claim 1, in which the matrix comprises a crystalline polyethylene glycol polymer and a polyethylene glycol stearate as a non-ionic emulsifier dispersed in the polyethylene glycol matrix in an amount of 2–50% by weight of the crystalline polymer and the non-ionic emulsifier, the non-ionic emulsifier having at least one domain which is compatible with the polyethylene glycol polymer and being selected from fatty acid esters and fatty alcohol ethers, the active substance being substantially homogeneously dispersed in the polyethylene glycol matrix and/or located in geometrically well-defined zones within the matrix, the non-ionic emulsifier and/or the active substance reducing the water affinity of domains between grains and in cracks in the crystalline polymer matrix and in the crystalline polymer matrix itself, thereby substantially eliminating water diffusion in the interface between the polymer crystals, so that erosion of the matrix is predominantly effected by the dissolving action of the aqueous medium on any matrix surfaces exposed to the medium.

22. A composition according to claim 1, wherein the matrix comprising the active substance comprises:
   e) a cellulose derivative which has thermoplastic properties and which is substantially insoluble in the aqueous medium in which the composition is to be used, and at least one of
   f) a cellulose derivative which is soluble or dispersible in water,
   g) a plasticizer, and
   h) a filler.

23. A composition according to claim 22, wherein said cellulose derivative of element e) is a cellulose ether that is shapeable by molding or extrusion when heated.

24. A composition according to claim 22, wherein the cellulose derivative of element e) is a cellulose ether comprising at least one ethylcellulose.

25. A composition according to claim 22, wherein the cellulose derivative of element e) is an ethylcellulose having an ethoxyl content in the range of 44.5–52.5%.

26. A composition according to claim 22, wherein the cellulose derivative of element e) is an ethylcellulose having an ethoxyl content in the range of 45.0–49.5%.

27. A composition according to claim 22, wherein the cellulose derivative of element e) is selected from the group consisting of cellulose acetate, cellulose propionate and cellulose nitrate.

28. A composition according to claim 22, wherein the cellulose derivative of element f) is selected from the group consisting of methylcellulose, carboxymethylcellulose and salts thereof, cellulose acetate phthalate, microcrystalline cellulose, ethylhydroxyethylcellulose, ethylmethylcellulose, hydroxyethylcellulose, hydroxyethylmethylcellulose, hydroxypropylcellulose, hydroxypropylmethylcellulose, hydroxymethylcellulose and hydroxymethylpropylcellulose.

29. A composition according to claim 22, wherein the cellulose derivative of element f) is a salt of carboxymethylcellulose which is selected from the group consisting of alkali metal and alkaline earth metal salts.

30. A composition according to claim 22, wherein the cellulose derivative of element f) is pharmaceutical quality hydroxypropylmethylcellulose.

31. A composition according to claim 22, wherein said plasticizer of element g) is selected from the group consisting of phosphate esters; phthalate esters; amides; mineral oils; fatty acids and esters thereof with polyethylene glycol, glycerin or sugars; fatty alcohols and ethers thereof with polyethylene glycol, glycerin or sugars; and vegetable oils.

32. A composition according to claim 22, wherein the plasticizer of element g) is a fatty alcohol which is selected from the group consisting of cetostearyl alcohol, cetyl alcohol, stearyl alcohol, oleyl alcohol and myristyl alcohol.

33. A composition according to claim 22, wherein the plasticizer of element g) is a non-ionic surfactant.

34. A composition according to claim 22, wherein said filler is selected from conventional tablet or capsule excipients.

35. A composition according to claim 22, in which said filler is selected from the group consisting of a diluent, a binder, a lubricant and a disintegrant.

36. A method for producing a composition for controlled delivery of at least one active substance into an aqueous medium by erosion of at least one surface of the composition, wherein said erosion occurs at a preprogrammed rate, the method comprising forming
   i) a matrix comprising the active substance, wherein the matrix is erodible in the aqueous medium in which the composition is used and wherein the matrix allows substantially no diffusion of water into the composition beyond any exposed surface layers of the matrix, and
   ii) a coating having at least one opening exposing at least one surface of said matrix, the coating comprising
      a) a first cellulose derivative which has thermoplastic properties and which is substantially insoluble in the aqueous medium in which the composition is used, and at least one of
      b) a second cellulose derivative which is soluble or dispersible in water,
      c) a plasticizer, and
      d) a filler,
wherein said coating crumbles and/or erodes upon exposure to the aqueous medium, at a rate which is equal to or slower than the rate at which the matrix erodes in the aqueous medium, allowing controlled exposure of said surface of the matrix to the aqueous medium, wherein said forming comprises extrusion molding or injection molding.

37. A method according to claim 36, wherein the composition is produced by co-extrusion of a) the matrix material with the active substance dispersed therein and b) the coating.

38. A method according to claim 36, wherein the composition is produced by injection moulding of the coating and subsequent injection moulding of the matrix containing the active substance.

39. A method according to claim 36, wherein the composition is produced by injection moulding of the coating and subsequent injection moulding of alternating layers comprising at least one layer comprising matrix material and at least one layer comprising the active substance.

40. A method according to claim 36, wherein the composition is produced by injection moulding of the matrix containing the active substance, or injection moulding of alternating layers comprising at least one layer comprising matrix material and at least one layer comprising the active substance, into a pre-formed tube which forms the coating.

41. A method according to claim 36, wherein the composition is formed by extrusion or injection moulding of the matrix containing the active substance followed by dip coating.

42. A composition according to claim 23, wherein said molding is injection molding, blow molding or compression molding.

43. A composition according to claim 1, wherein said aqueous medium is a body fluid.

44. A method according to claim 36, wherein said aqueous medium is a body fluid.

45. A composition for controlled delivery of at least one active substance into an aqueous medium by erosion of at least one surface of the composition, wherein said erosion occurrs at a preprogrammed rate, comprising
   i) a matrix comprising the active substance, and a crystalline polyethylene glycol polymer having at least one non-ionic emulsifier dispersed therein, wherein the matrix is erodible in the aqueous medium in which the composition is used, and
   ii) a coating having at least one opening exposing at least one surface of said matrix, the coating comprising
      a) a first cellulose derivative which has thermoplastic properties and which is substantially insoluble in the aqueous medium in which the composition is used,
   and at least one of
      b) a second cellulose derivative which is soluble or dispersible in water,
      c) a plasticizer, and
      d) a filler,
wherein said coating crumbles and/or erodes upon exposure to the aqueous medium, at a rate which is equal to or slower than the rate at which the matrix erodes in the aqueous medium, thereby allowing controlled exposure of said surface of the matrix to the aqueous medium.

46. A composition according to claim 45, wherein said aqueous medium is a body fluid.

47. A composition for controlled delivery of at least one active substance into an aqueous medium by erosion of at least one surface of the composition, wherein said erosion occurs at a preprogrammed rate, comprising
   i) a matrix comprising the active substance and a crystalline polyethylene glycol polymer having at least one non-ionic emulsifier dispersed therein, wherein the matrix is erodible in the aqueous medium in which the
   ii) a coating having at least one opening exposing at least one surface of said matrix, the coating comprising
      a) a first cellulose derivative which has thermoplastic properties and which is substantially insoluble in the aqueous medium in which the composition is to be used, said first cellulose derivative being a cellulose ether comprising at least one ethylcellulose,
   and at least one of
      b) a second cellulose derivative which is soluble or dispersible in water,
      c) a plasticizer, and
      d) a filler,
wherein said coating crumbles and/or erodes upon exposure to the aqueous medium, at a rate which is equal to or slower than the rate at which the matrix erodes in the aqueous medium, thereby allowing controlled exposure of said surface of the matrix to the aqueous medium.

* * * * *